United States Patent [19]

Keeley

[11] 4,239,918
[45] Dec. 16, 1980

[54] META, PARA-SUBSTITUTED ISOPROPYLIDENE BISPHENOLS AND METHODS FOR MAKING

[75] Inventor: Donald E. Keeley, Menlo Park, Calif.

[73] Assignee: General Electric Company, Schenectady, N.Y.

[21] Appl. No.: 966,895

[22] Filed: Dec. 6, 1978

[51] Int. Cl.$^3$ .................. C07C 43/205; C07C 39/16; C07C 41/00
[52] U.S. Cl. ................................ 568/640; 568/641; 568/722; 568/723; 568/726; 260/45.95 F; 260/45.95 G; 528/201
[58] Field of Search ............... 568/722, 723, 726, 640, 568/641

[56] References Cited

U.S. PATENT DOCUMENTS

| | | | |
|---|---|---|---|
| 2,464,207 | 3/1949 | Bender et al. | 568/723 X |
| 3,264,357 | 8/1966 | Webb et al. | 568/722 X |
| 3,359,281 | 12/1967 | Schlichting et al. | 568/722 X |
| 3,488,407 | 1/1970 | Schall et al. | 568/726 X |
| 3,758,597 | 9/1973 | Buysch et al. | 568/640 |

FOREIGN PATENT DOCUMENTS

| | | | |
|---|---|---|---|
| 1260478 | 2/1968 | Fed. Rep. of Germany | 568/722 |
| 963294 | 7/1964 | United Kingdom | 568/722 |

*Primary Examiner*—Bernard Helfin
*Attorney, Agent, or Firm*—William A. Teoli; James C. Davis, Jr.

[57] ABSTRACT

Meta,para-substituted isopropylidene bisphenols are provided and methods for making such materials. Phenol, or substituted phenol is condensed with a meta-substituted isopropenyl phenol or a meta-hydroxy-$\alpha,\alpha$-dimethylbenzyl alcohol in the presence of an acid catalyst. The resulting meta,para-substituted isopropylidene bisphenols can be used as stabilizers for polyvinyl chloride resins and as intermediates for making high performance thermoplastics having chemically combined meta,para-isopropylidene diphenoxy units.

7 Claims, No Drawings

META, PARA-SUBSTITUTED ISOPROPYLIDENE BISPHENOLS AND METHODS FOR MAKING

BACKGROUND OF THE INVENTION

It is generally recognized that bisphenols are important starting monomers for the synthesis of a variety of high performance thermoplastic polymers and resins. Bisphenol-A or 4,4'-isopropylidene diphenol of the formula,

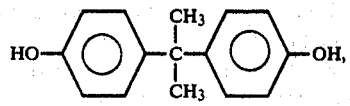
(1)

is generally synthesized from phenol and acetone using an acid catalyst. In addition to bisphenol-A of formula (1), 2,2-(2,4'-dihydroxydiphenol)propane or the "ortho" isomer of the formula

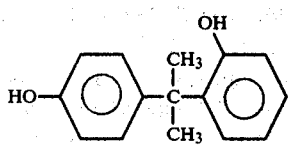
(2)

is also formed as a comonomer with bisphenol-A when the acetone process is employed, as taught, for example by Schlichting et al, U.S. Pat. No. 3,359,281.

An alternative procedure for making isopropylidene bisphenols which substantially eliminates any possibility of side reactions, as shown by the above described acetone process, is by the acid condensation of phenol with either the corresponding para-hydroxy-α,α-methylbenzyl alcohol, as shown by the following equation,

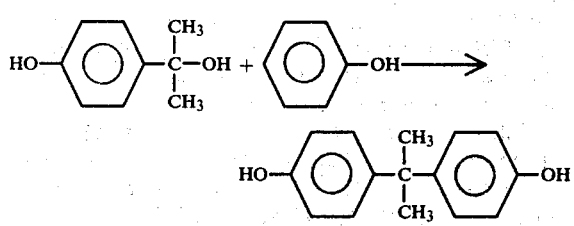

or by employing phenol with the corresponding isopropenyl phenol which is shown as follows:

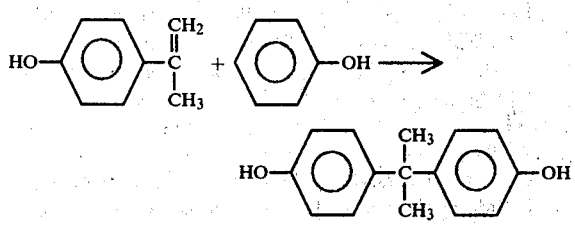

Experience has shown that the corresponding ortho-isomer of formula 2 cannot be made directly using either of the above alternative procedures. A self condensation of the corresponding ortho-hydroxybenzyl alcohol, or ortho-isopropenyl phenol, proceeds at a faster rate than the intercondensation with phenol.

SUMMARY OF THE INVENTION

The present invention is based on the discovery that meta,para-isopropylidene bisphenol-A of the formula,

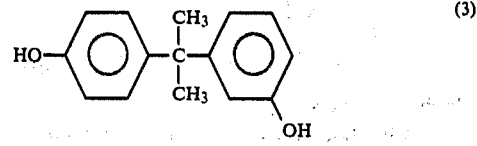
(3)

can be successfully made by an acid catalyzed condensation of phenol with either meta-isopropenyl phenol or meta-hydroxy-α,α-dimethylbenzyl alcohol. In addition, meta,para-isopropylidene bisphenol-A of the formula,

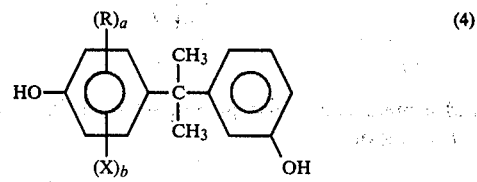
(4)

can be made by employing a substituted phenol in an acid catalyzed condensation with either meta-isopropenyl phenol, or metahydroxy-α,α-dimethylbenzyl alcohol as shown by the following equation,

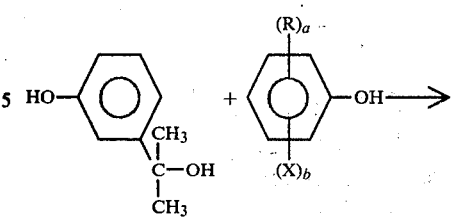

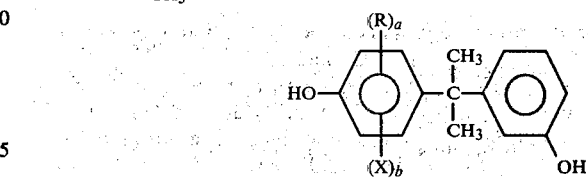

where R is a monovalent radical selected from $C_{(1-8)}$ alkyl radicals, $C_{(1-4)}$ alkoxy radicals, X is a halogen radical selected from chloro and bromo, a is a whole number having a value of from 0-3 inclusive and b is a whole number having a value of from 0-2 inclusive and the sum of a and b has a value of from 1-4 inclusive.

As shown in copending application Ser. No. 966,896, filed concurrently herewith and assigned to the same assignee as the present invention and now U.S. Pat. No. 4,237,259, the meta,para-isopropylidene bisphenol of formula (3) or analogs of formula (4) can be homopolymerized or copolymerized with other bisphenols or difunctional reactants to produce a variety of high performance thermoplastic organic polymers, such as polycarbonates, polyesters, polyester carbonates, polyformals, polyetherimides, polysulfones, epoxy resins and polycarbonate-polydiorganosiloxane block polymers.

DESCRIPTION OF THE INVENTION

There is provided by the present invention, a method for making a bisphenol of the formula,

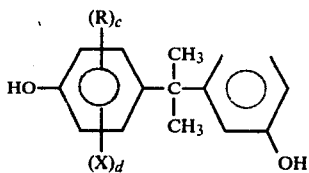 (5)

which comprises, (A) effecting reaction between a phenol of the formula,

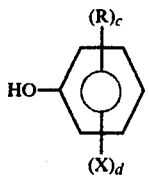

and a meta-substituted phenol selected from the class consisting of

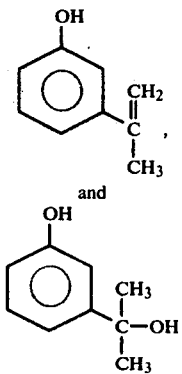

in the presence of an acid catalyst and at a temperature of from 0° C. to 100° C., and (B) recovering the bisphenol from the mixture of (1), where R and X are as previously defined, c is a whole number equal to 0 to 3 inclusive, d is a whole number equal to 0 to 2 inclusive and the sum of c and d is equal to 0 to 4 inclusive.

Bisphenols included by formulas (4) and (5) are, for example,

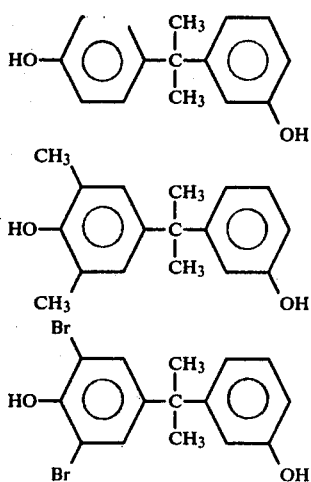

-continued

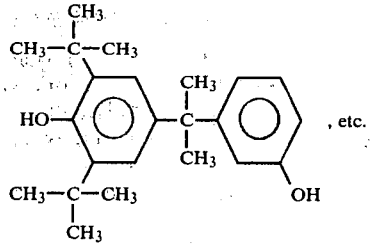, etc.

A method for making meta-isopropenyl phenol is shown by K. Auwers, Ann., 413, 253 (1917). Another procedure is shown by B. B. Corson et al, Preparation of Vinylphenol, Journal of Organic Chemistry, 23 544, (1958). Procedures for making meta-hydroxy-α,α-dimethylbenzyl alcohol is shown by Gilman et al Journal of Organic Chemistry, 19, p. 1057 (1954) based on the use of a methyl Grignard reagent with methyl m-hydroxy benzoate.

DETAILED DESCRIPTION OF THE INVENTION

In the practice of the invention, the condensation is effected between "phenol", which hereinafter includes phenol and substituted phenols as previously described, and the "meta-substituted phenol", which hereinafter includes meta-isopropenyl phenol, and meta-dimethylcarbinol hydroxy benzene or meta-hydroxy-α,α-dimethylbenzyl alcohol. Reaction can be effected at ambient temperatures in the presence of suitable organic solvent, or it can be effected in the absence of an organic solvent at temperatures above the melting point of phenol, such as 50° C. to 100° C., which can serve as both a reactant and solvent for the aforementioned meta-isopropenyl phenol or meta-dimethylcarbinol hydroxy benzene. In addition, the reaction can be conducted in the presence of an acid catalyst.

A more ratio of 1.0 to 10 moles of phenol, per mole of meta-substituted phenol can be used and preferably 1 to 3 moles of phenol, per mole of meta-substituted phenol.

Suitable organic solvents which can be employed under ambient conditions are, for example, toluene, chlorobenzene, etc. Suitable acid catalysts which can be used as sulfuric acid, hydrochloric acid, hydrogen chloride gas which can be employed under pressure, boron trifluoride, hydrogen fluoride, trifluoroacetic acid, acidified clays, acid ion exchange resin beds for the passage of phenol and meta-substituted phenol. Agitation of the reactants to facilitate reaction can be accomplished with standard means such as stirrer, etc. Reaction can be achieved over a period of from 1 to 30 minutes, depending upon the nature of the reactants, and such factors as the degree of agitation, whether a solvent is used, temperature, etc.

The meta,para-isopropylidene bisphenol can be recovered as a crude product from the reaction mixture or it can be recrystallized in accordance with a standard technique from solvents such as water, hydrocarbons, alcohols, water alcohol mixtures, etc.

In order that those skilled in the art will be better able to to practice the present invention, the following examples are given by way of illustration and not by way of limitation. All parts are by weight.

EXAMPLE 1

A mixture of 5 parts of phenol and 1 part of meta-isopropenyl phenol in 21 parts of toluene was added dropwise to about 5 parts of 75% aqueous sulfuric acid solution. When the addition was completed, the reaction mixture was stirred an additional 5 minutes and diluted with 35 parts of diethylether to produce a two phase mixture. The organic layer was separated and washed with 25 parts of a saturated aqueous sodium bicarbonate solution, dried over magnesium sulfate and concentrated under reduced pressure to produce a brown oil. The oil was recrystallized from chloroform. There was obtained about an 80% yield of a white powder having a melting point of 97°-98° C. Based on method of preparation and its NMR spectrum, the product was meta,-para-isopropylidene bisphenol having the formula,

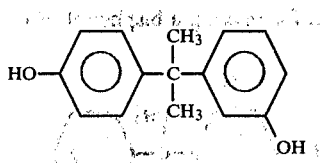

The above bisphenol is blended with a polyvinyl chloride resin along with sufficient dioctylphthalate and a dry base lead stabilizer EXL of the National Lead Company, on a roll mill to produce a plasticized blend having ½% by weight of the bisphenol and about 3% by weight of lead stabilizer. Several 4½ inch by 4½ inch by 75 mil test slabs are prepared. Additional test slabs free of the bisphenol are prepared by the same procedure. The test slabs are then placed in a circulating air oven at 121° C. for a period of 4 weeks. It is found that the test slabs free of the bisphenol have darkened considerably and have generally changed in physical characteristics based on a failure to resist the effect of heat-aging. This shows that the bisphenol exhibits valuable stabilizing characteristics for polyvinyl chloride resins.

It is further found that the meta,para-bisphenol-A is a white crystalline solid and is soluble in several solvents such as methylene chloride, chloroform and toluene in which the corresponding para,para-bisphenol-A of formula (1) is only slightly soluble. As a result of this improved showing of solubility, it is found that the meta,-para-bisphenol-A is capable of being converted to a polycarbonate in a highly efficient manner as compared to the para,para-bisphenol-A as shown by the following:

A mixture of 2 parts of meta,para-bisphenol-A, 13.5 parts of methylene chloride, 7 parts of water, about 0.04 part of triethylamine and 0.016 part of phenol is phosgenated over a 20 minute period. There is added to the mixture during the phosgenation 1.9 part of phosgene and enough 20% by weight of aqueous sodium hydroxide solution to maintain the mixture at a pH at 10-12. After the phosgenation the mixture is flushed with nitrogen and washed with about 25 parts of 10% hydrochloric acid. The polycarbonate is precipitated in a blender with about 80 parts of methanol and collected by suction filtration and dried under vacuum at 65° C. for 18 hours. There is obtained a polycarbonate having an average molecular weight of about 70,000, a number average molecular weight of about 17,000 and a glass transition temperature of 112° C.

EXAMPLE 2

A mixture of 5 parts of phenol, 1.14 part of meta-hydroxy-α,α-dimethylbenzyl alcohol in 20 parts of toluene was added dropwise to about 5 parts of 75% aqueous sulfuric acid. When the addition was completed, the reaction mixture was then stirred an additional 5 minutes, diluted with 35 parts of diethyl ether and the layers separated. The organic layer was washed with about 25 parts of a saturated aqueous sodium bicarbonate solution, dried over magnesium sulfate, and concentrated under reduced pressure to provide a brown oil. The oil was crystallized from chloroform. There was obtained an 81% yield of white powder having a melting point of 97°-98° C. Based on method of preparation the product was meta,para-bisphenol-A. Its identity was further identified by its IR spectrum.

EXAMPLE 3

There was added a solution of 0.1 part of meta-hydroxy-α,α-dimethylbenzyl alcohol, 0.5 part of 2,6-xylenol and about 4 parts of toluene to about 5 parts of a 75% aqueous solution of sulfuric acid. The addition was completed dropwise and the mixture was stirred constantly during the addition. After the addition was completed, separation of the organic phase and the aqueous phase was allowed to occur. The aqueous phase was extracted with about 35 parts of diethylether. The organic layers were then combined and dried with anhydrous magnesium sulfate. The resulting dried mixture was then concentrated by stripping the mixture of solvent under reduced pressure. The resulting material was then eluted in the form of a methylene chloride solution using silica gel chromatography resulting in a 79% yield of product having a melting point of 126°-127° C. Based on method of preparation and its infrared spectrum, the product was a bisphenol of the formula,

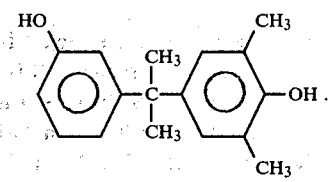

The above compound is roll milled with polyvinyl chloride resin and a lead stabilizer in accordance with the procedure of Example 1 to produce test slabs. It is found that the above bisphenol imparts improved stability to polyvinyl chloride resin. In addition, the above bisphenol is used to make high molecular weight polycarbonate by phosgenating a methylene chloride solution in the presence of triethylamine as described in Example 1.

EXAMPLE 4

A solution of 0.1 part meta-hydroxy-α,α-dimethylbenzyl alcohol and 0.5 part of 2,6-dimethoxyphenol in about 4 parts of toluene is added dropwise with stirring to about 5 parts of a 75% aqueous sulfuric acid solution. After the addition was completed, the layers were allowed to separate and the aqueous layer was extracted with about 35 parts of diethylether. The combined organic layers were then dried with magnesium sulfate and dried under reduced pressure. After the crude product was crystallized from hexane there was obtained a tan solid having a melting point of 138°–140° C. having the formula,

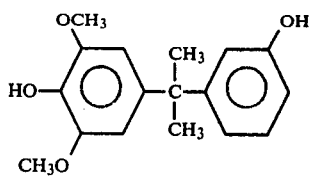

The above bisphenol is roll milled with polyvinyl chloride, plasticizer and lead stabilizer in accordance with the procedure of Example 1 to produce test slabs. After heat-aging in accordance with the procedure of Example 1, it is found that the bisphenol is a valuable stabilizer for polyvinyl chloride resins. The bisphenol is also used to make a polycarbonate polymer following the procedure of Example 1.

Although the above examples are directed to only a few of the very many variables within the scope of the present invention, it should be understood that the present invention is directed to a much broader class of meta,para-isopropylidene bisphenols as shown by the description preceding these examples.

What I claim as new and desire to secure by Letters Patent of the United States is:

1. Bisphenols of the formula,

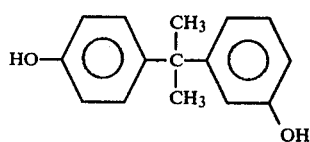

where R is a monovalent radical selected from $C_{(1-8)}$ alkyl radicals, and $C_{(1-4)}$ alkoxy radicals, X is a halogen radical selected from chloro and bromo, a is a whole number having a value of from 0 to 3 inclusive, b is a whole number having a value of 0 to 2 inclusive and the sum of a+b has a value of 0 to 4 inclusive.

2. A bisphenol of the formula,

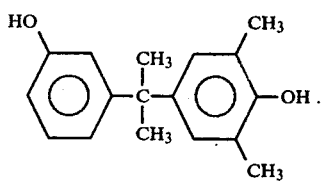

3. A bisphenol of the formula,

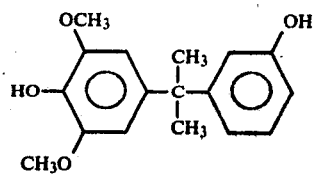

4. A bisphenol of the formula,

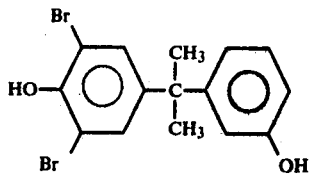

5. A bisphenol of the formula,

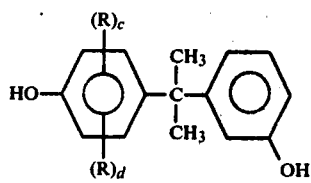

6. A method for making a bisphenol of the formula,

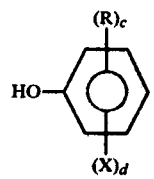

which comprises (A) effecting reaction between a phenol of the formula,

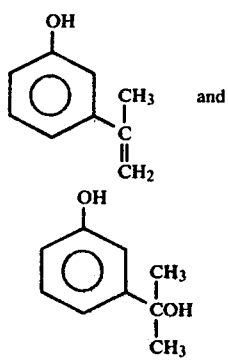

and a meta-substituted phenol selected from the class consisting of in the presence of an acid catalyst and at a temperature of from 0° C. to 100° C., and (B) recovering the bisphenol from the mixture of (1), where R is a monovalent radical selected from $C_{(1-8)}$ alkyl radicals $C_{(1-4)}$ alkoxy radicals, X is a halogen radical selected from chloro and bromo, c is a whole number equal to 0 to 3 inclusive, d is a whole number equal to 0 to 2 inclusive and the sum of c and d is equal to 0 to 4 inclusive.

7. A method for making meta,para-bisphenol-A of the formula,
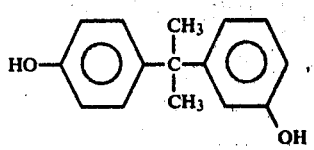
which comprises
(a) effecting contact between phenol and a meta-substituted phenol selected from,
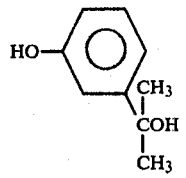
and
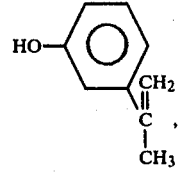
(b) recovering the meta, para-bisphenol from (a).
* * * * *